United States Patent
Chung et al.

(10) Patent No.: US 7,132,103 B2
(45) Date of Patent: *Nov. 7, 2006

(54) EFFECTS OF SPORODERM-BROKEN GERMINATION ACTIVATED GANODERMA SPORES ON TREATMENT OF SPINAL CORD INJURY

(75) Inventors: Chee-Keung Chung, Mongkok (HK); Siu-Kan Tong, Mongkok (HK)

(73) Assignee: Enhan Technology Holdings International Co., Ltd., Kowloon (HK)

( * ) Notice: Subject to any disclaimer, the term of this patent is extended or adjusted under 35 U.S.C. 154(b) by 341 days.

This patent is subject to a terminal disclaimer.

(21) Appl. No.: 10/631,809

(22) Filed: Aug. 1, 2003

(65) Prior Publication Data
US 2005/0025785 A1  Feb. 3, 2005

(51) Int. Cl.
*A61K 35/84* (2006.01)

(52) U.S. Cl. .................................. 424/195.15
(58) Field of Classification Search ............. 424/195.15
See application file for complete search history.

(56) References Cited

U.S. PATENT DOCUMENTS

| 6,143,714 | A | 11/2000 | Wong et al. |
| 6,288,069 | B1 | 9/2001 | Glasky |
| 6,291,493 | B1 | 9/2001 | Farooque et al. |
| 6,464,982 | B1 * | 10/2002 | Lam .................... 424/195.15 |

FOREIGN PATENT DOCUMENTS

| CN | 1101860 | * | 4/1995 |
| CN | 1111529 | * | 11/1995 |

OTHER PUBLICATIONS

China Daily Business Weekly. Nov. 3, 1997. "Paralysis Drug", CIN Abstract., 1 page.*
Dorland's Medical Dictionary. 1988, 27th ed. pp. 1224–1226 concerning the medical definition of "paralysis".*
Zhao et al. J. Pharmacol. Sci. 2004. vol. 95, No. 2, pp. 294–298, BIOSIS Abstract enclosed.*
Cheung, William M.W., et al.; Ganoderma extract activates MAP kinases and induces the neuronal differentiation of rat pheochromocytoma PC12 cells; Federation of European Biochemical Societies, vol. 486, 2000, p. 291–296.
Metz, Gerlinde A.S.,; Validation of the Weight–Drop Contusion Model in Rats: A Comoparative Study of Human Spinal Cord Injury; Journal of Neurotrauma, vol. 17, No. 1, 2000, p. 1–17.

* cited by examiner

*Primary Examiner*—Christopher R. Tate
(74) *Attorney, Agent, or Firm*—Fei-Fei Chao; Bingham McCutchen LLP

(57) ABSTRACT

The present invention provides a method for treating patients with spinal cord injury by administering germination activated *Ganoderma lucidum* spores (GASP) to the patients. The GASP are sporoderm-broken. The GASP promote axon regeneration and improve motor neuron survival in the injured spinal cord.

22 Claims, 9 Drawing Sheets

(9 of 9 Drawing Sheet(s) Filed in Color)

VR cut (A)

(B)

(A)

(B)

Sciatic nerve cut-----6W    SN cut (A)

(B)

EFFECTS OF SPORODERM-BROKEN GERMINATION ACTIVATED GANODERMA SPORES ON TREATMENT OF SPINAL CORD INJURY

FIELD OF THE INVENTION

The present invention relates to a method for treating a mammal having spinal cord injury by administering to the mammal sporoderm-broken germination activated *ganoderma* spores (GASP). The GASP are particularly effective in promoting regeneration of the axons and improving survival of the motor neurons within the spinal cord.

BACKGROUND OF THE INVENTION

The spinal cord coordinates the body's movement and sensation to and from the brain. It is a complex organ containing nerve cells (also known as neurons), and supporting cells (also known as neuroglial cells or glial cells). A typical neuron consists of a cell body, containing the nucleus and the surrounding cytoplasm (perikaryon); several short radiating processes (dendrites); and one long process (the axon, which terminates in twiglike branches (telodendrons) and may have branches (collaterals) projecting along its course. The axon together with its covering or sheath forms the nerve fiber. The neuroglial or glial cells form the supporting structure of nervous tissue. There are three types of glial cells, which are astrocytes, oligodendrocytes, and microglia. Astrocytes and oligodendrocytes (collectively macroglia) are of ectodermal origin. These cells far outnumber neurons in the brain and spinal cord and perform many essential functions. The oligodendrocyte creates the myelin sheaths that insulate axons and improve the speed and reliability of nerve signal transmission. Astrocytes, large star-shaped glial cells, regulate the composition of the fluids that surround neurons. Some of these cells also form scar tissue after injury. Microglia are of mesodermal origin. They are smaller cells that become activated in response to injury and help clean up waste products. All of these glial cells produce substances that support neuron survival and influence axon growth.

There are several types of neurons that lie within the spinal cord and carry out the spinal cord functions. Large motor neurons have long axons that control skeletal muscles in the neck, torso, and limbs. Sensory neurons (also called dorsal root ganglion cells) have axons which carry information from the body into the spinal cord. Spinal interneurons, which lie completely within the spinal cord, help integrate sensory information and generate coordinated signals that control muscles.

Motor neurons are traditionally classified as upper motor neurons or lower motor neurons. Upper motor neurons reside in the precentral gyrus of the brain, and send long processes down to synapse on lower motor neurons in the ventral (anterior) horns of the grey matter of the spinal cord. From the ventral horns of the spinal cord, axon processes of lower motor neurons coalesce to form the ventral roots. These axons eventually terminate on one or more muscle fibers. Through arborization of the terminal part of its fiber, each lower motor neuron comes in contact with anywhere from a few to 100–200 or more muscle fibers to form a "motor unit," (Adams and Victor, 1985, in "Principles of Neurology," McGraw-Hill, Inc., New York, p. 37).

Many axons in the spinal cord are covered by sheaths of an insulating substance called myelin, which gives them a whitish appearance; therefore, the region in which they lie is called "white matter." The neurons themselves, with their tree-like dendrites that receive signals from other neurons, make up "gray matter." This gray matter lies in a butterfly-shaped region in the center of the spinal cord. Like the brain, the spinal cord is enclosed in three membranes (meninges): the pia mater, the arachnoid, and the dura mater. The spinal cord is then surrounded by rings of bone called vertebra.

The spinal cord and the brain together make up the central nervous system (CNS). Unlike neurons of the peripheral nervous system (PNS), which carry signals to the limbs, torso, and other parts of the body, it is generally believe that neurons of the CNS do not regenerate after injury. (Walker, *New Eng. J. Med.*, (1991) 324: 1885–1887). Recent research, however, supports that the injured spinal cord can be successfully regenerated, provided that the damaged neurons must be able to survive the injury or be replaced, and the axons must be able to regrow and find appropriate targets. Axons and their targets must then interact to construct synapses, the specialized structures that act as the functional connections between neurons.

The spinal cord is about 18 inches long and extends from the base of the brain, down the middle of the back, to about the waist. The spinal cord is organized into segments along its length. The spinal nerves that branch out from the spinal cord to the other parts of the body are lower motor neurons (LMNs). Thirty-one pairs of spinal nerves exit and enter at each vertebral level and communicate with specific areas of the body. The segments in the neck, or cervical region, referred to as C1 through C8, control signals to the neck, arms, and hands. Those in the thoracic or upper back region (T1 through T12) relay signals to the torso and some parts of the arms. Those in the upper lumbar or mid-back region just below the ribs (L1 through L5) control signals to the hips and legs. Finally, the sacral segments (S1 through S5) lie just below the lumbar segments in the mid-back and control signals to the groin, toes, and some parts of the legs. The effects of spinal cord injury at different segments reflect this organization.

Neurons of the brain and spinal cord respond to signals differently from most other cells of the body, including those in the peripheral nervous system (PNS). The brain and spinal cord (i.e., the CNS) are confined within bony cavities that protect them, but also render them vulnerable to compression damage caused by swelling or forceful injury. Cells of the CNS have a very high rate of metabolism and rely upon blood glucose for energy. The "safety factor," that is the extent to which normal blood flow exceeds the minimum required for healthy functioning, is much smaller in the CNS than in other tissues. For these reasons, CNS cells are particularly vulnerable to reductions in blood flow (ischemia). Other unique features of the CNS are the "blood-brain-barrier" and the "blood-spinal-cord barrier." These barriers, formed by cells lining blood vessels in the CNS, protect neurons by restricting entry of potentially harmful substances and cells of the immune system. Trauma may compromise these barriers, perhaps contributing to further damage in the brain and spinal cord. The blood-spinal-cord barrier also prevents entry of some potentially therapeutic drugs. Finally, in the brain and spinal cord, the glial cells and the extracellular matrix (the material that surrounds cells) differ from those in peripheral nerves. Each of these differences between the PNS and CNS contributes to their different responses to injury.

Although spinal cord is well protected, spinal cord injury does occur due to causes such as trauma (e.g., car accident, violence, falls, sports) and disease (e.g., polio, spina bifida, Friedreich's Ataxia). In the United States, approximately 450,000 people live with spinal cord injury, and there are about 10,000 new cases every year, mostly involving males between ages of 16 to 30. Spinal cord injury can be divided into complete injury (no motor and sensory functions below the level of the injury) and incomplete injury (some functioning below the primary level of injury). Recovery from spinal cord injury is much more difficult because the neurons are very specialized and unable to divide and create new cells.

Usually, injuries to the spinal cord do not result in a cut through the cord; instead, they crush the axons. Researchers studying spinal cords obtained from autopsy have identified several different types of spinal cord injuries. The most common types of spinal cord injuries are contusions (bruising of the spinal cord) and compression injuries (caused by pressure on the spinal cord). Other types of injury included lacerations, caused by a bullet or other object, and central cord syndrome.

The damage that occurs to spinal cord axons within the first few hours after-injury is complex and it occurs in stages. The normal blood flow is disrupted, which causes oxygen deprivation to some of the tissues of the spinal cord. Bleeding into the injured area leads to swelling, which can further compress and damage spinal cord axons. The chemical environment becomes destructive, due primarily to the release of highly reactive molecules, e.g., free radicals. These molecules break up cell membranes, including killing cells that were not injured initially. Macrophages that invade the site of injury to clean up debris may also damage uninjured tissue. Non-neuronal cells, such as astrocytes, may divide too often, forming a scar that impedes the regrowth of the injured nerve cell axons.

The early events that follow a spinal cord injury can lead to other kinds of damage later on. Within weeks or months, cysts may form at the site of injury which fill with cerebrospinal fluid. Typically, scar tissue develops around the cysts, creating permanent cavities that can elongate and further damage neurons. Also, nerve cell axons that were not damaged initially often lose their myelin. Over time, these and other events can contribute to more tissue degeneration and a greater loss of function.

Effective drug therapy for spinal cord injury first became a realty in 1990s, when methylprednisolone, the first drug shown to improve recovery from spinal cord injury, moved from clinical trials to standard use. The NASCIS II (National Acute Spinal cord Injury Study II) trial, a multicenter clinical trial comparing methylprednisolone to placebo and to the drug naloxone, showed that methylprednisolone given within 8 hours after injury significantly improves recovery in humans. Completely paralyzed patients given methylprednisolone recovered an average of about 20% of their lost motor function, compared to 8% recovery of function in untreated patients. Partially paralyzed patients recovered an average of 75% of their function, compared to 59% in people who did not receive the drug. Patients treated with naloxone, or treated with methylprednisolone more than 8 hours after injury, did not improve significantly more than patients given a placebo. (National Institutes of Health, "Spinal Cord Injury: Emerging Concepts," (1996) www.ninds.nih.gov/health_and _medical/pubs). The results of the clinical trial of methylprednisolone revolutionized thinking that there is a window of opportunity for acute treatment of spinal cord injury.

Today, more drugs are being tested for treatment of spinal cord injury. For example, U.S. Pat. No. 6,291,493 discloses the use of clomethiazole (5-(2-chloroethyl)-4-methylthiazole) for treating pathological conditions caused by compression to the spinal cord, whether traumatically induced or due to compression caused by tumours, haemorrhage, infectious processes or spinal stenosis. U.S. Pat. No. 6,288,069 discloses the use of 9-substituted hypoxanthine derivatives (such as N-4-carboxyphenyl-3-(6-oxohydropurin-9-yl) propanamide) to stimulate regeneration or survival of a mammalian motor neuron or of a mammalian sensory neuron. U.S. Pat. No. 6,143,714 discloses the use of a hepatocyte growth factor (HGF) to promote the survival, growth and differentiation of motor neurons.

Recently, Cheung et al. (*FEBS Lett* 2000; 486(3): 291–6) disclose that *Ganoderma lucidum* extract induces neuronal differentiation in vitro, using a primary neuronal cell system (i.e., PC12 cells). The PC12 cells are derived from rat pheochromocytoma cells which respond to the nerve growth factor (NGF). The *Ganoderma ludicum* extract described by Cheung et al. is made from the fruit bodies of the *Ganoderma lucidum*.

In the invention to be presented in the following sections, a novel use of the sporoderm-broken germination-activated *Ganoderma* spores (GASP) from *Ganoderma lucidium* for treatment of spinal cord injury is undertaken. The GASP have previously been disclosed for use in treating patients with cancer, AIDS, hepatitis, diabetes, and cardiovascular diseases, and can prevent or inhibit free radical oxidation and hepatotoxic effects. See U.S. Pat. Nos. 6,316,002 and 6,468,542, which are incorporated herein by reference. Unlike methylprednisolone, which has to be given to patients within 8 hours after injury to be effective, the GASP can be administered to humans and animals in a much later time while still achieving significant, improvement. A further benefit of using the GASP is that they are non-toxic so that higher dosage can be prescribed to the patients.

SUMMARY OF THE INVENTION

The present invention provides an effective method for treating spinal cord injury by administering an effective amount of germination activated *Ganoderma* spores (GASP) into a mammal, preferably human, after a spinal cord injury. The GASP are sporoderm-broken. The GASP are preferred to be orally administered to the mammal within about 1 day of said spinal cord injury.

The causes of the spinal cord injury include compression or severance of the spinal cord (such as severance of the ventral root of the spinal cord, or severance or crush of the sciatic nerve), trauma (such as car accident, violence, falls, sports etc.), or a disease (such as polio, spina bifida, or Friedreich's Ataxia). In addition, the spinal cord injury can be due to damage or death of neurons within the injured spinal cord or crush of axons within the injured spinal cord.

The GASP are preferred to be orally administered to a mammal, including a human, in the amount of about 0.5–15 g per kg of body weight per day, most favorably about 8 g per kg of body weight per day.

The present invention also provides a method for improving survival of neurons, particularly motor neurons, after a spinal cord injury by administering an effective amount of the GASP to a mammal, preferably a human, whose spinal cord has been injured. The GASP are sporoderm-broken. It is preferred that the GASP is administered to the mammal within 1 day of the spinal cord injury. The effective amount of the said GASP is about 0.5–15 g per kg of body weight per day, preferably 8 g per kg of body weight per day.

In another embodiment, a method for promoting axon regeneration after a spinal cord injury is provided, which requires the administration, preferably oral administration of an effective amount of the GASP to a mammal, preferably a human, who has a spinal cord injury. The GASP are sporoderm-broken. The GASP are preferred to be orally administered to the mammal within 1 day after the spinal cord injury. The GASP are preferred to be administered to the mammal in the amount of about 0.5–15 g per kg of body weight per day, most favorably about 8 g per kg of body weight per day.

BRIEF DESCRIPTION OF DRAWINGS

The patent or application file contains at least one drawing executed in color. Copies of this patent or patent application publication with color drawings will be provided by the U.S. Patent and Trademark Office upon request and payment of the necessary fee.

DETAILED DESCRIPTION OF THE INVENTION

Figure 1:
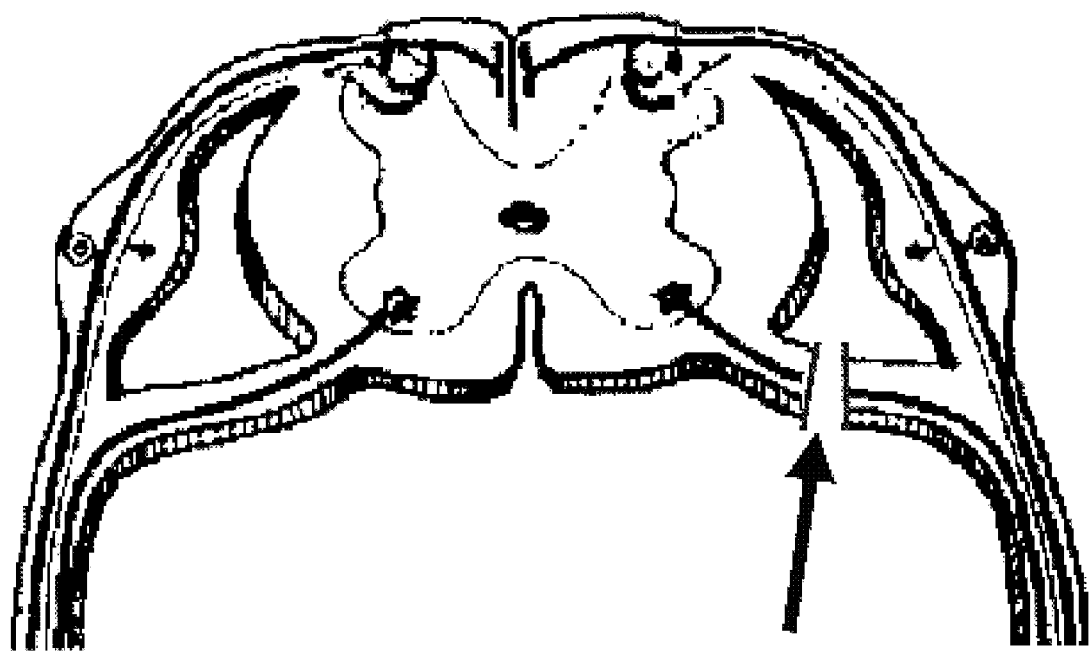
FIG. 1 shows the ventral root cut-off site in the right side L3, L4, and L5 nerves of the animal model used in Examples 1 and; 2.

The present invention provides a method for effective treatment of spinal cord injury. The method involves administering an effective amount of germination activated *Ganoderma* spore powder (GASP) into a mammal having spinal cord injury.

*Ganoderma* (*Ganoderma lucidum* Leyss ex Fr. Karst) is a polyporous fungus which belongs to the class Basidiomycetes, the family Polypolaceae, and the genus *Ganoderma*. *Ganoderma* spores are tiny and mist-like spores of 5~8 μm in sizes which have extremely hard and resilient, double-layer epispores, thus making them difficult to break open. The spores contain high concentrations of many bioactive substances, including, but are not limited to, polyunsaturated fatty acids, polysaccharides, vitamins, sterols, trace minerals, amino acids, and triterpenes. The GASP used in the present invention are sporoderm-broken (i.e., the double-layer epispores of the spores are broken so that the bioactive substances within the spores are released), which is produced by the method described in U.S. Pat. No. 6,316,002 (the '002 patent). The entire content of the '002 patent is herein incorporated by reference. Through the unique spore-breaking method described in the '002 patent, the bioactive substances within the GASP are recovered in high yields and the functional activities of the bioactive substances are successfully preserved.

As shown below is a general description of the method used in the '002 patent, which leads to the production of the GASP:

I. Soaking to induce germination: Mature and perfect spores of *Ganoderma lucidum* were carefully selected to carry out a soaking process to induce germination. Spores were kept in clear or distilled water, biological saline solution, or other nutritional solutions that could enable the spores of *Ganoderma lucidum* to germinate rapidly. Examples of nutritional solutions include coconut juice or a 1–5% malt extract solution, 0.5–25% extracts of *Ganoderma lucidum* sporocarps or *Ganoderma lucidum* capillitia, 0.1–5% of culture solution containing biotin, 0.1–3% of culture solution containing monobasic potassium phosphate and magnesium sulfate. The choice of solution would depend on the soaking time required, the amount of spores to be processed and other such factors as availability of materials. One or more of the above germination solutions could be used, with the amount added being 0.1–5 times the weight of the spores of *Ganoderma lucidum*. The soaking time can be determined according to the temperature of the water, and usually the soaking was carried out for 30 min to 8 h with the temperature of the water at 20–43° C. Preferably soaking times were 2–4 hours, and temperature of the water was 25–35° C.

II. Activation culture The spores of *Ganoderma lucidum* were removed from the soaking solution and excess water was eliminated by allowing it to drip. The spores were then placed in a well-ventilated culturing box at a constant temperature and humidity so that spore activation culture could be carried out. The relative humidity of the culture was generally set at 65–98%, the culture temperature at 18–48° C. and the activation time lasted from 30 min to 24 h. Preferably humidity is 85–97% and temperature is 25–35° C. Using the method provided by the present invention, the activation of spores of *Ganoderma lucidum* reached a rate of more than 95%. During activation, the cell walls of the spores of red *Ganoderma lucidum* were clearly softened such that it was easier to penetrate the cell walls of the spores.

III. Treatment of the epispores: After the germination activation process, the spores were treated by enzymolysis. This process was carried out at a low temperature and under conditions such that enzyme activity was maintained, using chitinase, cellulase, or other enzymes, which are commonly used in the industry. The process was complete when the epispores lost their resilience and became brittle. Alternatively, physical treatments were carried out to penetrate the cell walls, for example, micronization, roll pressing, grinding, super high pressure microstream treatment, and other mechanical methods commonly used in the industry could be carried out, with a penetration rate of over 99%.

IV. Drying or extraction: Drying was carried out at low temperature using standard methods including freeze-drying or vacuum-drying etc., which are commonly used in the industry. The obtained product had a moisture content less than 4%. After drying, the bioactive substances were extracted by water or alcohol, or by thin film condensation. The extracted bioactive substances could be further purified by dialysis to ensure no contamination in the final products.

V. Pharmaceutical formulations of the bioactive substances: The bioactive substances can then be made into purified powders, extract pastes, solutions for injection, or for oral consumption. The invention also encompasses the manufacture of pharmaceutical preparations of the active substances, using well-known expedients and methods of manufacture known in the art. In addition, the bioactive substances can be dosed by any convenient method including tablets, capsules, solutions, suppositories, nasal sprays, paranterals, or injection devices. The choice of method for administration is determined by the clinical situation of the patient. The bioactive substances of the present invention, produced by the methods described, include active genes; inducers of the biotic potential promotor, inducers of the multicellular activator, inducers of interferon, lactone A, *ganoderma* polysaccharide, *ganoderma* spore fatty acids, *ganoderma* spore long chain alkyl hydrocarbon, *ganoderma* triterpenes, sterols, superoxide dismutase, vitamin E, active glycoprotein, certain growth factors, *ganoderma* acid A, superoxide dismutases (SOD), active glycoproteins, multiple active enzymes, and growth factors and so on. These bioactive substances, in a whole, contribute to the therapeutic uses described in the later sections.

The present invention is conducted using a rat model. According to Metz et al. (*J Neurotrauma* (2000): 17(1): 1–17), which is herein incorporated by reference, the functional, electrophysiological and morphological outcome parameters following spinal cord injury in rats can be extrapolated for those in humans. Metz et al. collected data from human patients with chronic spinal cord injury and compared them to those of rats with contusion spinal cord injury induced by a weight-drop. The results suggest an analogous relationship in rats and humans with respect to functional, electrophysiological, and morphological outcomes, which demonstrates that rat can serve as an adequate animal model for research on functional and morphological changes after spinal cord injury and the effects of new treatment strategies.

GASP are non-toxic. The preferred method for administering GASP is through oral uptake. Currently, GASP are approved by the Food and Drug Administration (FDA) to be used as dietary supplement in the capsule form under the name of Enhanvol® and Holistol, sold by Enhan Technology Holdings International Company, Ltd. in Hong Kong. Each capsule of GASP contains 0.3 g of GASP. The recommended dosage of GASP, when used as dietary supplement, is 4 times every day, 4 capsules each time. Thus, for an adult of 60 kg, the daily dosage of GASP as dietary supplement is at about 0.08 g/kg of body weight per day.

It has been shown, however, that no physiological and pathological abnormalities were found when 8 g/kg/day of GASP were given to patients and animals. In the present invention, 0.5 g to 15 g/kg/day of GASP have been given to animals and demonstrated significant effects on treatment of spinal cord injury. However, it is understood that the dosage for any particular patient depends upon a variety of factors, including age, body weight, general health, sex, diet, time of administration, route of administration, rate of excretion, drug combination and the severity of the disease. For these reasons, dosing is left to the discretion of the skilled clinician.

The following examples are illustrative, but not limiting the scope of the present invention. Reasonable variations, such as those occur to reasonable artisan, can be made herein without departing from the scope of the present invention.

EXAMPLE 1

Effects of GASP on Survival of Lumbar Motor Neurons

Animal Model:

Healthy SD rats supplied by the Guangdong Medical Animals Center with body weights of approximately 100 g were selected.

Method:

The SD rats were divided into 2 groups, i.e., the GASP treatment group and the control group. In each rat, the right side of the ventral roots at the L3, L4, and L5 lumbar nerves was cut off. (See FIG. 1). The left side of the ventral roots was left untouched to be used for comparison.

GASP (20 g) was dissolved in 100 mL of 0.5% sodium carboxymethyl cellulose to a final concentration of 20%. After the ventral roots were cut off for about one day, the rats in the GASP treatment group were fed approximately 2 mL of GASP solution twice daily via gavage for 35 days. Daily dose of GASP was 8 g/kg/day. The rats in the control group were fed the same amount of 0.5% sodium carboxymethyl cellulose twice daily for 35 days. All rats were kept under the same condition.

At the end of the treatment period, nerve tissues were collected from both groups. Segments of spinal cord were fixed using 4% paraformaldehyde, soaked in a 30% sugar cane in phosphate buffered saline (PBS) solution, and frozen-sectioned to slices of 30 μm thickness. Every fifth slice was selected and a total of 10 slices were stained with neutral red. The survival neurons were stained red in the sectioned slices and were counted according to the method of Clarke and Oppenheim. For each rat, the survival motor neurons on the 10 nerve, slices were averaged.

Statistical analysis was performed using T-test.

Figure 2:
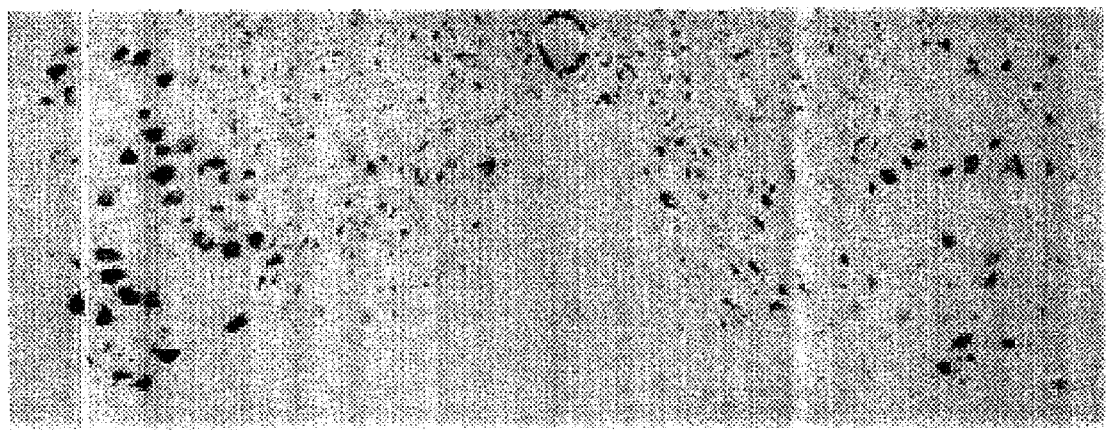
FIG. 2 shows the images of the spinal cord stained with neutral red 35 days after the right side ventral roots were cut-off. Survival motor neurons were stained red and showed up as purplish spots against the blue background in these images. As shown in the control group (A), the number of survival motor neurons in the injured (right) side was markedly less than that of the uninjured (left) side. As shown in the GASP treatment group (B), the number of the survival motor neurons at the injured (right) and uninjured (left) sides was statistically insignificant, indicating that the GASP were effective in promoting lumbar motor neuron survival after a spinal cord injury due to cut-off of the ventral roots.
Figure 2:
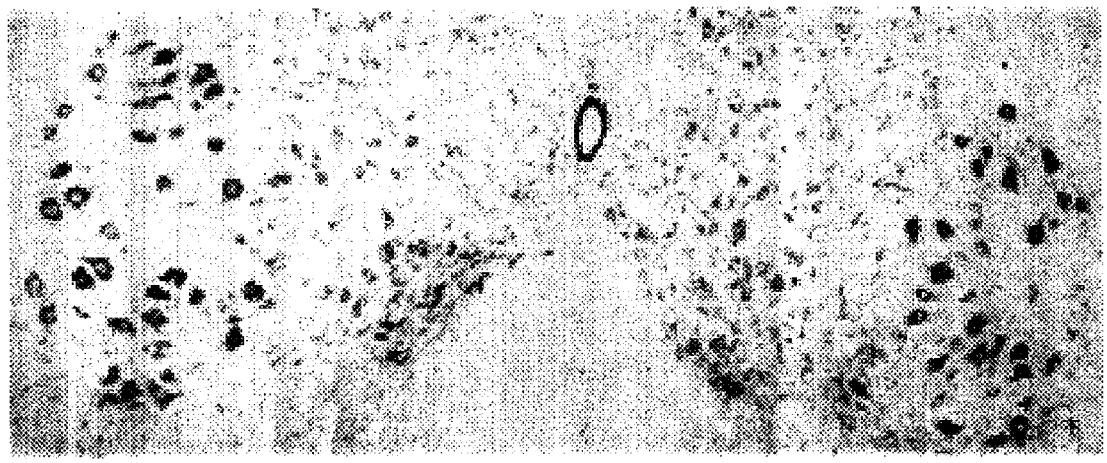

Results:

The results are shown in Table 1 and FIG. 2.

```
bound(e) = e is not equal to Ø
interior (e) = dest(e) is not equal to v∞
boundary (e) = dest(e) is equal to V∞
AddTriangle(v₀,v₁,v₂)
{
    for(i ← 0, . . .,2) {
        e ← getRep(vᵢ);
        if (bound(e)) {
            a ← b ← c ← Ø;
            e₀ ← e;
            do {
                w ← dest(e);
                if(w = vᵢ₋₁) {
                    if (right(e) ≠ v∞)
                        Error("invalid edge");
                    b ← e;
                }
                else if (w = vᵢ₊₁) {
                    if (left(e) ≠ v∞)
                        Error("invalid edge");
                    a ← e;
                }
                else if(w = v∞) c ← e;
                e ← onext(e);
            } while (e ≠ e₀ and not (bound(a) and bound(b)));
            g₁ ← Ø;
            if (bound(a)) {
                if (bound(b)) {
                    if (onext(a) ≠ oprev(b)) {
                        e ← onext(b);
                        while ((e ≠ a) and (dest(e) ≠ v∞))
                            e ← onext(e);
                        if(e = a)
                            Error("non-manifold vertex");
                        f ← oprev(b);
                        Splice(onext(a),f);
                        Splice(e,f);
                    }
                    gᵢ ← b;
                }
                else gᵢ ← onext(a);
            }
            else if (bound(b)) gᵢ ← b;
            else if (bound(c)) gᵢ ← c;
            else Error("non-manifold vertex");
        }
    }
    i ← 0;
    repeat {
        if (not(interior(gᵢ)) and not(interior(gᵢ₋₁))) {
            e ← MakeEdge(vᵢ,vᵢ₋₁);
            if (boundary(gᵢ)) Splice(onext(e),gᵢ);
            if (boundary(gᵢ₋₁)) Splice(rot⁻¹(e),gᵢ₋₁);
            gᵢ₋₁ ← rot⁻¹(e);
            gᵢ ← e;
        }
        else if (interior(gᵢ) and interior(gᵢ₋₁)) {
            Swap(rot⁻¹(gᵢ));
            if (interior(gᵢ₊₁)) {
                Splice(rot⁻¹(gᵢ),gᵢ₊₁);
                DestroyEdge(gᵢ₊₁);
            }
            setRep(vᵢ,gᵢ);
            setRep(vᵢ₊₁,rot(gᵢ));
            setRep(vᵢ₊₂,rot⁻¹(gᵢ));
            return;
        }
        i ← i+1
    }
}
```

The results show that the numbers of survived motor neurons at the uninjured sides in both groups were similar. However, the number of survived motor neurons at the injured side without treatment after the cut-off of the L3, L4 and L5 nerves was significantly lower (6.43±1.49), as compared to the uninjured side (15.02±0.86) and the injured side of the GASP treatment group (13.61±0.74). The % survival rate of the GASP treatment group was 90%, which was significantly higher than that of the control group (57%). Similar findings were observed in the neural red stains of the spinal, cord tissues (FIG. 2).

These results indicated that 35 days of the GASP treatment at 8 g/kg/day was effective in promoting the survival of lumbar motor neurons to 90% survival in rats after their ventral roots were cut off.

Conclusion:

It had been demonstrated that GASP was effective in promoting the survival of motor neurons after a severance type of nerve injury.

EXAMPLE 2

Effects of GASP on Lumbar Motor Neuron Survival

The activity of neuronal nitric oxide synthase (nNOS) in the injured neurons signifies with the survival of the motor neurons. The histochemical nicotinamide adenine dinucleotide phosphate-diaphorase (NADPH-d) reaction is considered a suitable marker for nNOS activity. Thus, the measure of the activity of nNOS using the NADPH-d staining method can be used to determine the survival of the motor neurons.

Method:

Animal models were prepared, grouped and treated as described in Example 1, supra.

After 14 days of treatment, five (5) rats from each group were sacrificed and their respective nerve tissues were collected. The remaining rats in each group were continued to be fed with their daily dosage of GASP or sodium carboxymethyl cellulose solution until day 35. These rats were then sacrificed and the nerve tissues were collected.

Segments of spinal cord tissues were fixed using 4% paraformaldehyde, soaked in a phosphate buffered saline solution (PBS) containing 30% sugar cane, and frozen-sectioned to 30 μm thickness for use on slides. The selected nerve tissue sections were incubated in an NADPH solution and incubated for 1–3 hours, washed and then re-stained with 1% neutral red.

Statistical analysis of the treatment and control groups was performed using T-test.

Figure 3:
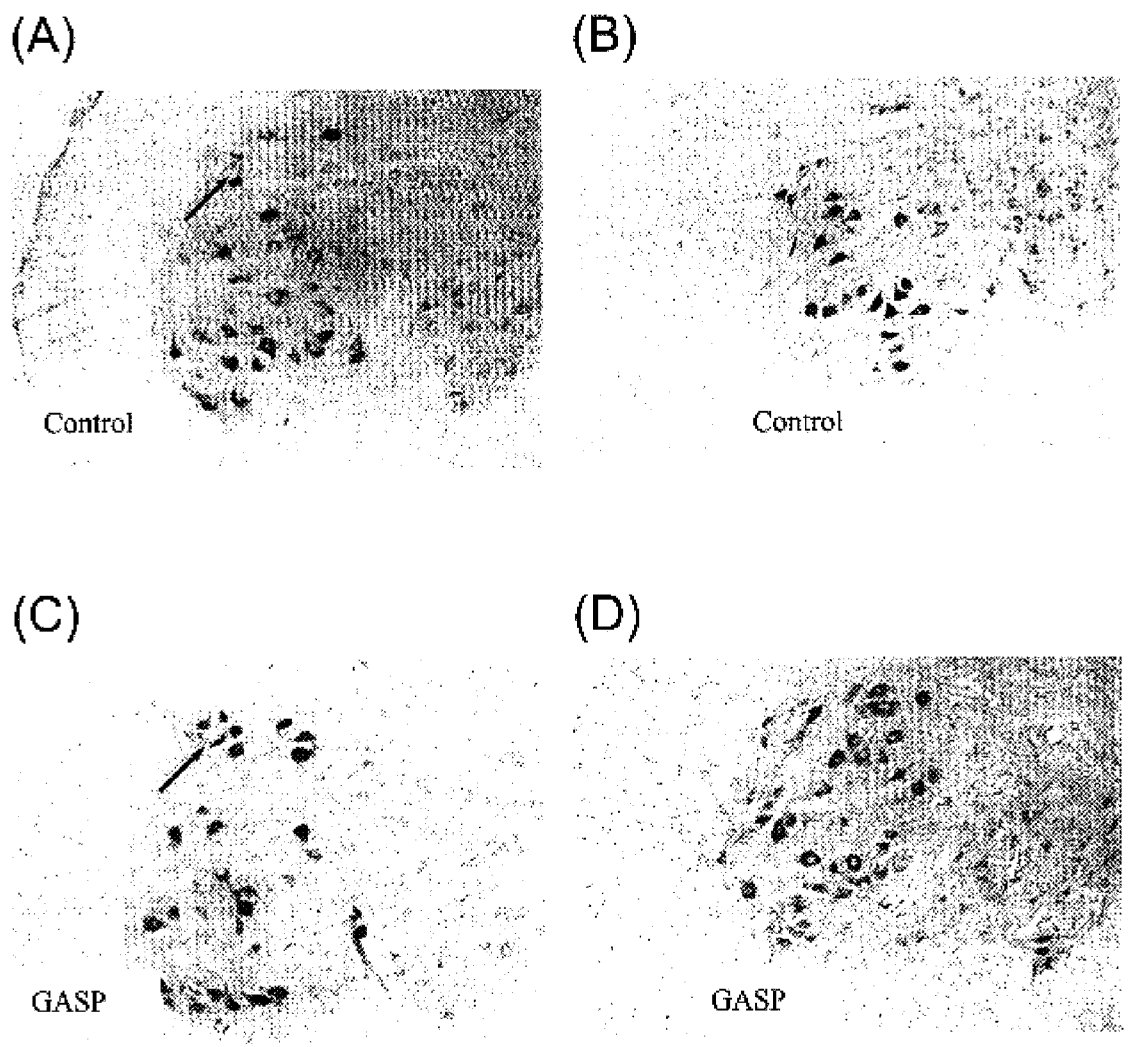
FIG. 3 shows the images of the nerve tissues, which were first stained with nicotinamide adenine dinucleotide phosphate-diaphorase (NADPH-d) and re-stained with neutral red. Images (A) and (B) are nerve tissues of rats in the control group at 14 and 35 days after ventral root cut-off, respectively. Images (C) and (D) are nerve tissues of rats in the GASP treatment group at 14 and 35 days after the cut-off of the ventral roots, respectively. Survival motor neurons were stained with neutral red. Arrows in images (A) and (C) are directed to neurons that were positive for neuronal nitric oxide synthase (nNOS) activity and were stained in a purple color. At 14 days after the cut-off of the ventral roots, there were a high number of nNOS-positive neurons in the nerve tissues of the GASP treatment group (C) than the control group (A), indicating that the GASP were effective in promoting motor neuron survival after spinal cord injury.
Figure 4:
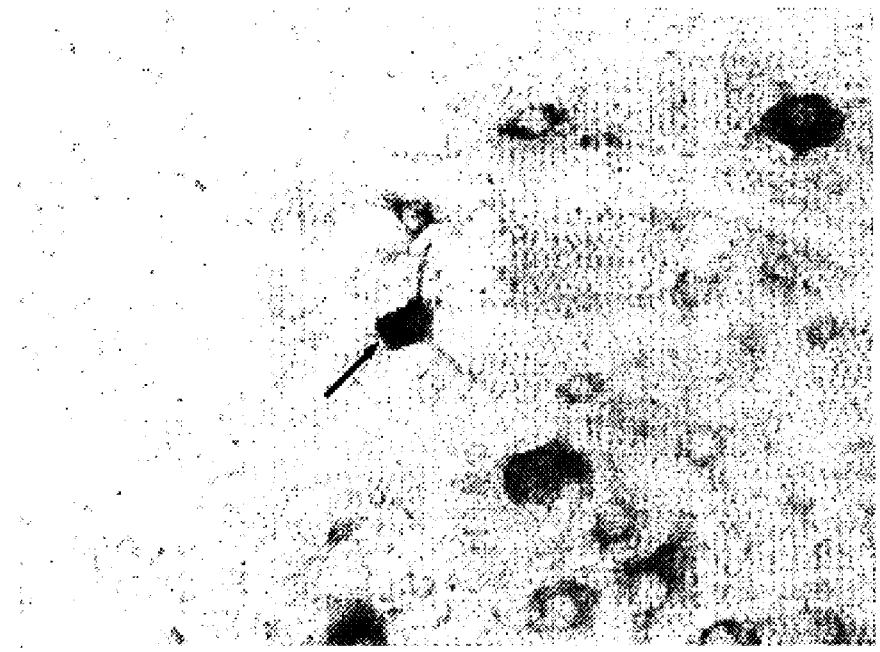
FIG. 4 shows the images of nerve tissues (at 100× magnification), which were first stained with NADPH-d, and then re-stained with neutral red. Images (A) and (B) are nerve tissues of rats in the control and GASP treatment groups at 14 days after the cutoff of the ventral roots, respectively. Survival motor neurons were stained with neutral red. Arrows in the images are directed to neurons that were positive for nNOS activity and were stained in a purple color.
Figure 4:
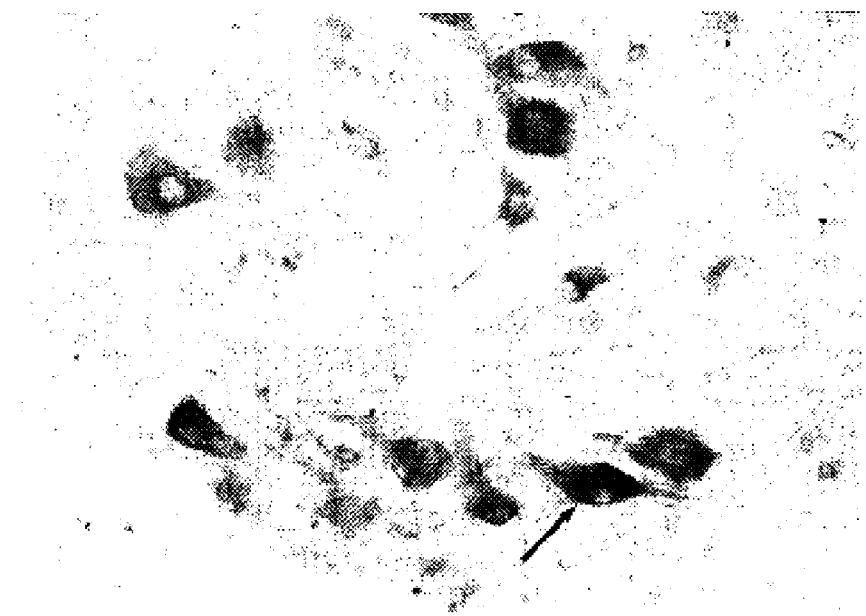

Results:

The results of the nNOS activity in the nerve tissues are shown in Table 2 and FIGS. 3 and 4.

TABLE 2

Effects of the GASP on Motor Neuron Survival After Lumbar Ventral Roots Being Cut-off for 14 Days

| | Control group (n = 5) | GASP treatment group (n = 5) | P* |
|---|---|---|---|
| Number of survived motor neurons at the uninjured (left) side | 13.69 ± 0.70 | 15.26 ± 0.30 | |
| Number of nNOS-positive neurons at the injured (right) side | 1.41 ± 0.26 | 5.55 ± 0.60 | |
| % nNOS-positive at the injured (right) side** | 10.36 ± 1.85 | 38.29 ± 4.37 | <0.01 |

*p value denotes comparison between the control and the GASP treatment groups.
**% nNOS-positive was determined as the percent ratio of the number of nNOS-positive neurons to that of the survived motor neurons at the injured (right) side of the ventral roots.

As shown in Table 2 and FIGS. 3 and 4, at 14 days after the cut-off of the ventral roots, the number of survived motor neurons (stained in red) at the uninjured side of the control group was similar to that of the GASP treatment group. However, the number of nNOS-positive neurons (stained in purple) of the control group was markedly less than that of the GASP treatment group. As shown in FIGS. 3(B) and 3(D), there were more survived motor neurons in the GASP treatment group (D) than those in the control group (B). The results suggest that the GASP had positive effects on promoting the survival of the motor neurons after the nerves at the ventral roots were cut-off.

Conclusion:

It had been demonstrated that the GASP were effective in promoting the survival of the neurons after a severance type of spinal cord nerve injury

EXAMPLE 3

Effects of the GASP on Regeneration of Injured Axons

Figure 5:
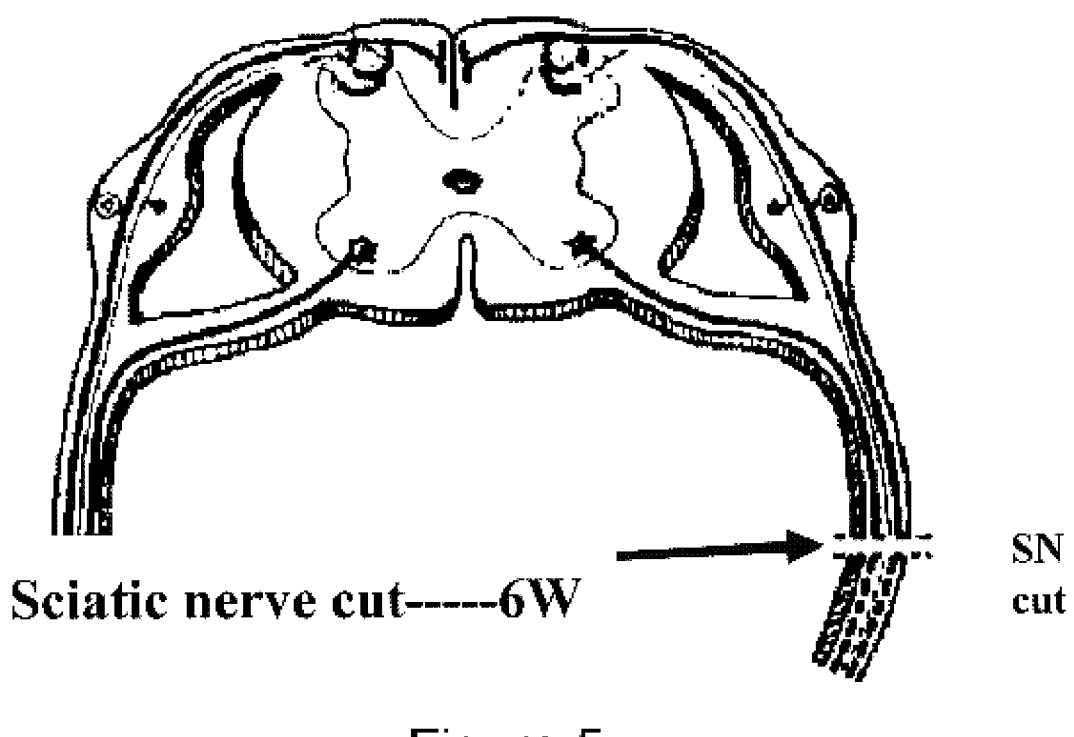
FIG. 5 shows the cut-off site in the right side sciatic nerve of the animal model used in Examples 3–6.

Animal Model:

A rat sciatic, nerve cut-off/re-stitched model was used in this study. Briefly, a section of the right side sciatic nerve of the experimental animal was exposed and cut off as shown in FIG. 5. The epineurium layers of the two open ends of sciatic nerve were then microsurgically stitched together to give an animal model that mimics cut/crush types of injury. The left side sciatic nerve was left untouched to be used for comparison to the injured side.

Method:

Animal models were prepared as shown in Examples 1–2, supra, and divided into 2 groups, the GASP treatment and the control groups.

GASP (20 g) was dissolved in 100 mL of 0.5% sodium carboxymethyl cellulose to a final concentration of 20%. The rats in the GASP treatment group were fed approximately 2 mL of GASP solution twice daily via gavage. Daily dose of GASP was 8 g/kg/day; The rats in the control group were fed the same amount of 0.5% sodium carboxymethyl cellulose twice daily. All rats were kept under the same conditions.

Fluorogold (FG), a retrograde fluorescent tracer, was used to track the regeneration of the axons. 2.5 μL of 3% FG solution were injected using a microinjector into the sciatic nerves at both injured (right) and uninjured (left) sides. At the injured (right) side, FG was injected at 5 mm distal to the site of injury. The L4 spinal cords were then removed from the experimental rats, frozen-sectioned and studied under fluorescence microscope. "FG %" was calculated as the percent ratio of the number of FG-positive neurons at the injured side to that of the uninjured side of the same animal.

Figure 6:
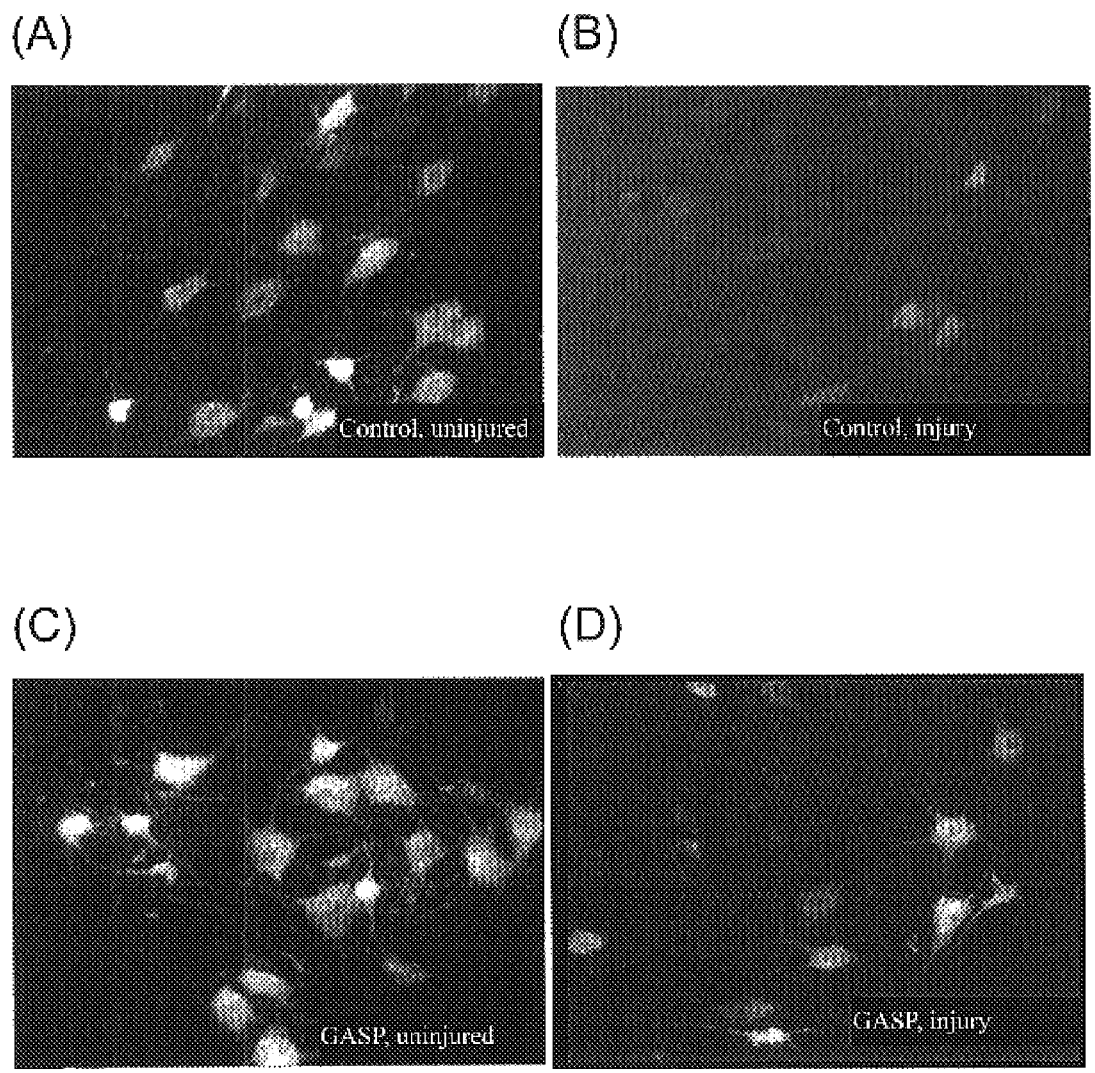
FIG. 6 are the images of L4 spinal cord sections labeled with a retrograde tracer Fluorogold (FG) after the right side sciatic nerve was cut-off, followed by perineurium layers re-stitched. Images (A) and (B), respectively, show the uninjured (left) and injured (right) sides of the control group. Images (C) and (D), respectively, show the uninjured (left) and injured (right) sides of the GASP treatment group. The numbers of FG-labeled neurons at the uninjured sides of both groups (see (A) and (C)) were compared. The FG-labeled neurons in the injured side of the control group (B) appeared to be much less than that of the GASP treatment group (D), indicating that the GASP were effective in promoting the regeneration of the injured motor neuron axons.

Statistical analysis was performed using T test,

Results:

The results of the axon regeneration studies using FG are shown in Table 3 and FIG. 6.

```
RemoveTriangle(t)
{
    for (i = 0, . . .,2) {
        e ← {t,i};
        h₁ ← oprev(e);
        vᵢ ← org(e);
        if (right(hᵢ) = v∞)
            if(oprev(hᵢ) = onext(e)))
                setRep(vᵢ,Ø);
            else
                setRep(vᵢ,oprev(oprev(hᵢ)));
        else
            setRep(vᵢ,hᵢ);
    }
    if ((right(h₀) ≠ v∞) and
        (right(h₁) ≠ v∞) and
        (right(h₂) ≠ v∞)) {
            e ← MakeEdge(v₀,v₁);
            Splice(h₀,e);
            h₀ ← e;
    }
    i ← Ø;
    repeat {
        if (right(hᵢ) = v∞) {
            Swap(hᵢ);
            if (right(hᵢ₊₁) = v∞) {
                e ← sym(hᵢ₊₁);
                Splice(oprev(hᵢ₊₁),rot⁻¹(e));
                Splice(oprev(e),onext(e));
                DestroyEdge(hᵢ₊₁);
            }
            if (right(hᵢ₋₁) = v∞) {
                e ← sym(hᵢ₋₁);
                Splice(oprev(hᵢ₋₁),rot⁻¹(e));
                Splice(oprev(e),onext(e));
                DestroyEdge(hᵢ₋₁);
            }
            return;
        }
        i ← i+1;
    }
}
```

FG is a retrograde fluorescence tracer. It was injected at the distal side of the cut-off/re-stitched injury, thus the detection of the FG-labeled neurons in the spinal cord region was indicative to axon regeneration.

As shown in Table 3 and FIG. 6, the numbers of FG-labeled neurons at the uninjured sides of both groups were similar, contrasting to the numbers of the FG-labeled neurons at the injured sides of both groups, which were significantly lower. However, the FG-labeled neurons at the injured side of the GASP group demonstrated a significant greater number than those at the injured side of the control group.

Based on counting of the FG-labeled neurons at the injured and the uninjured sides of the sciatic nerves, the regeneration rate (%) of the axons can be determined by dividing the number of the FG-labeled neurons at the injured side of the sciatic nerve by the number of the FG-labeled neurons at the uninjured side of the sciatic nerve in the same animal. Under this calculation, the regeneration rate of the axons was about 18% in the control group and about 59% in the GASP treatment group.

Conclusion:

It had been demonstrated that the GASP was effective in treating crush injuries of the spinal cord, particularly in promoting the regeneration of the axons.

EXAMPLE 4

Electrophysiology Effects of the GASP on Regeneration of the Injured Axons

Method:

The animal models were prepared and treated as described in Example 3, supra.

After 6 weeks of treatment with or without GASP, the rats were anaesthetized and the sciatic and sural nerves were exposed. An electrical stimulator was attached mesially to the repaired side and the recording electrode was placed at the distal side. After the electrical stimulation, the electrical impulse traveling along the nerve was traced and recorded. The same procedure was repeated at the uninjured side. Transduction speeds of the injured and uninjured sciatic nerves were determined. The ratio of the transduction speed of the injured side to that of the uninjured side was used as a marker for axon regeneration. The peak-to-peak values of the electrical impulse traveling along the nerves at the injured and uninjured sides were determined and used as an indicator for axon regeneration.

Statistical analysis was performed using T-test.

Figure 7:
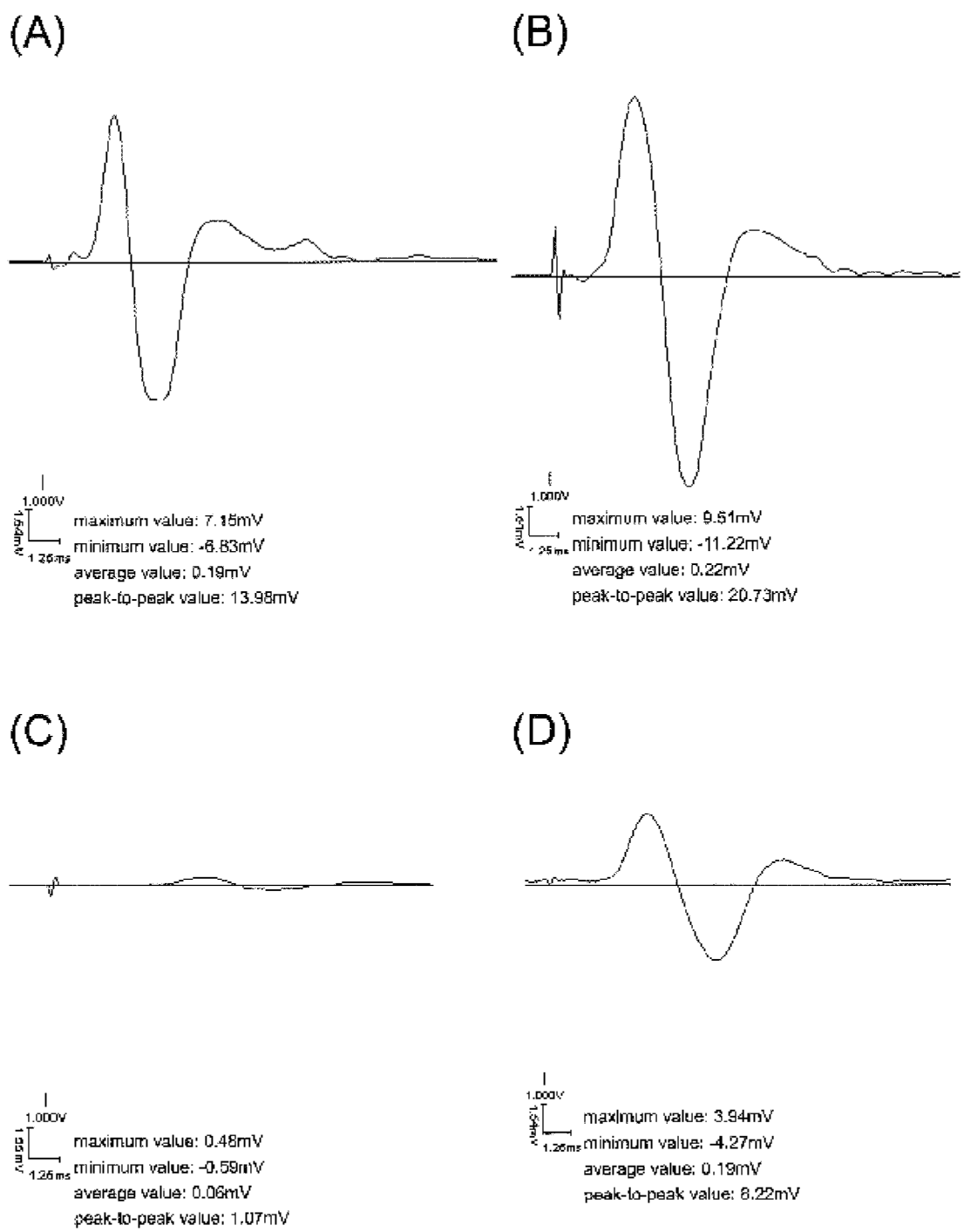
FIG. 7 shows the transduction diagrams of the sciatic nerves at the uninjured side (A) and the injured side (C) of the control group and the uninjured side (B) and the injured side (D) of the GASP treatment group, after the right side sciatic nerve was cut-off and re-stitched. The peak-to-peak value and the electrical impulse transduction speed of the electrical impulses were determined. When diagrams (C) and (D) were compared, the peak-to-peak value and the impulse transduction in diagram (D) were higher and faster, indicated that the GASP treatment improved the electrical impulse transduction in the injured sciatic nerve. This suggests that a 6-week GASP treatment was effective in promoting the regeneration of the axons in the injured sciatic nerve.

Results:

The results are shown in Table, 4 and FIG. 7.

```
struct Mesh
{
    Vertex[]    vertices;
    Edge[]      representatives;
    Triangle[]  triangles;
    Triedge[]   triedges
    uint32      numVertices;
    uint32      numTriangles;
    uint32      numInterior;
    uint32      numBoundary;
};
```

After the sciatic nerve was cut off and its outer layers stitched together, the transduction of an electrical impulse alone the nerve across the site of injury was indicative of the regeneration of the nerve axons. As shown in Table 4 and FIGS. 7(A) and 7(B), the transduction of the electrical impulses at the uninjured sides of both groups were similar in terms of the peak-to-peak values and the transduction speed. However, at the injured side of the control group, the transduction of an electrical stimulation almost completely ceased (Table 4, FIG. 7(C)). In comparison, about 40% of the electrical stimulation traveled along the sciatic nerve across the site of injury at a slightly slower speed at the injured side of the GASP treatment group. These results indicated that the GASP treatment at 8 g/kg/day for 6 weeks was effective in promoting axon regeneration in rats after the sciatic nerve was cut-off and the outer layers re-stitched.

Conclusion:

It has been demonstrated that GASP was effective in promoting axon regeneration in a crush type of spinal cord injury,

EXAMPLE 5

Effects of GASP on Regeneration of Injured Axons

Method:

The animal models were prepared and treated as described in Example 3, supra.

After 6 weeks of treatment with or without the GASP, the calf muscles (*musculus peronaeus longus*) were removed from both of the injured and uninjured sides of each rat. The isolated muscles were weighed and recorded. The muscle atrophy of the isolated muscles was determined. The isolated muscles were then stained with Hematoxylin and Eosin (H&E stain) for use in histology study.

Figure 8:
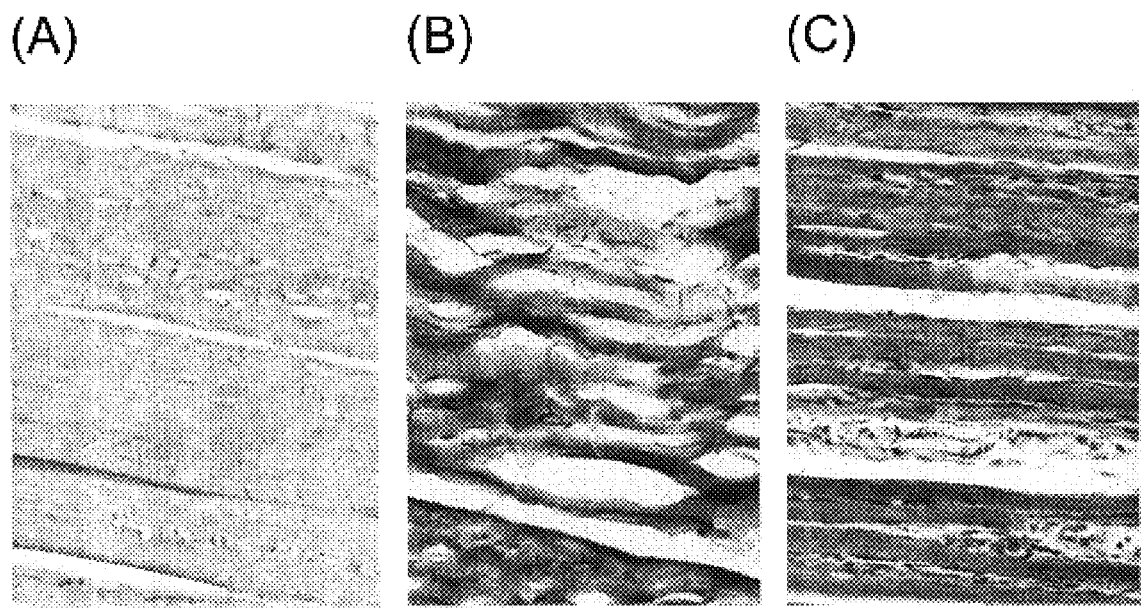
FIG. 8 shows the Hematoxylin and Eosin (H&E) stains of normal calf muscle (A); calf muscle of the control group after the sciatic nerve was cut-off for 6 weeks (B); and calf muscle of the GASP treatment group after the sciatic nerve was cut-off for 6 weeks (C). Normal calf muscle tissue exhibited a regular, smooth, and parallel pattern as shown in (A). The calf muscle of the control group (B) exhibited marked irregularity, while the calf muscle of the GASP treatment group (C) retained most of the normal pattern. This suggests that the GASP preserved the calf muscle after the spinal cord injury.

Results:

Marked muscle atrophy and weight reduction were observed in the calf muscles isolated from the injured side of the control group. As shown in FIG. 8(A), normal calf muscle tissue exhibited a regular, smooth, and parallel pattern. The calf muscle of the control group (FIG. 8(B)) exhibited marked irregularity, while the calf muscle of the GASP treatment group (FIG. 8(C)) retained most of the normal pattern. This suggests that the GASP had the effects of preserving the calf muscle after the nerve injury.

Conclusion:

It had been demonstrated that the GASP promoted muscle preservation after spinal cord nerve injury.

EXAMPLE 6

Effects of the GASP on Regeneration of Nerve Fibers in the Injured Axons

Method:

The animal models were prepared and treated as described in Example 3, supra.

After 6 weeks of treatment, the sciatic nerve axons were removed from both the injured and uninjured sides of each rat. The isolated nerve tissues were fixed, sectioned and then stained with Mallory's stain.

Figure 9:
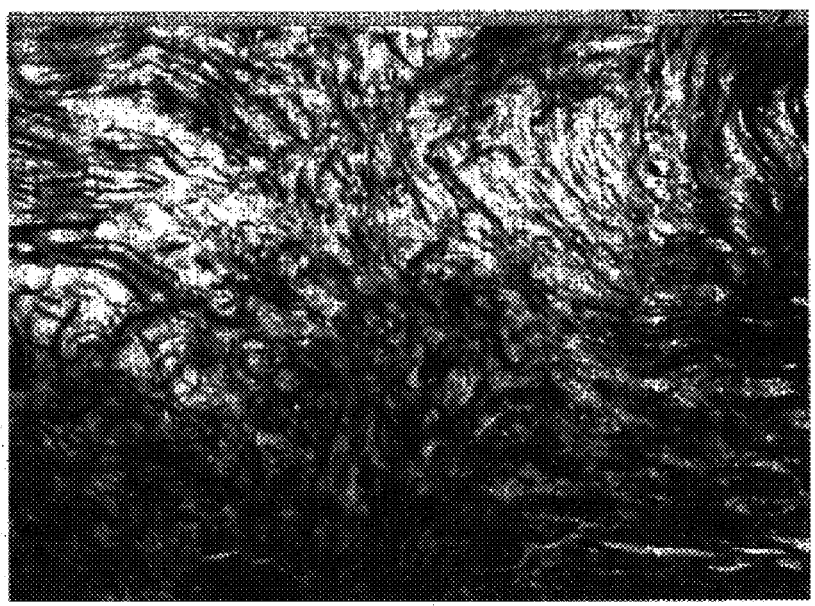
FIG. 9 shows the Mallory's stains of repaired sciatic nerve tissues in the control group (A) and the GASP treatment group (B) after the cut-off of the sciatic nerve. Red stain indicated nerve fiber regeneration, which was mostly seen in the nerve tissues of the GASP treatment group (B) and markedly less in that of the control group (A). This indicates that GASP were effective in promoting nerve fiber regeneration.
Figure 9:
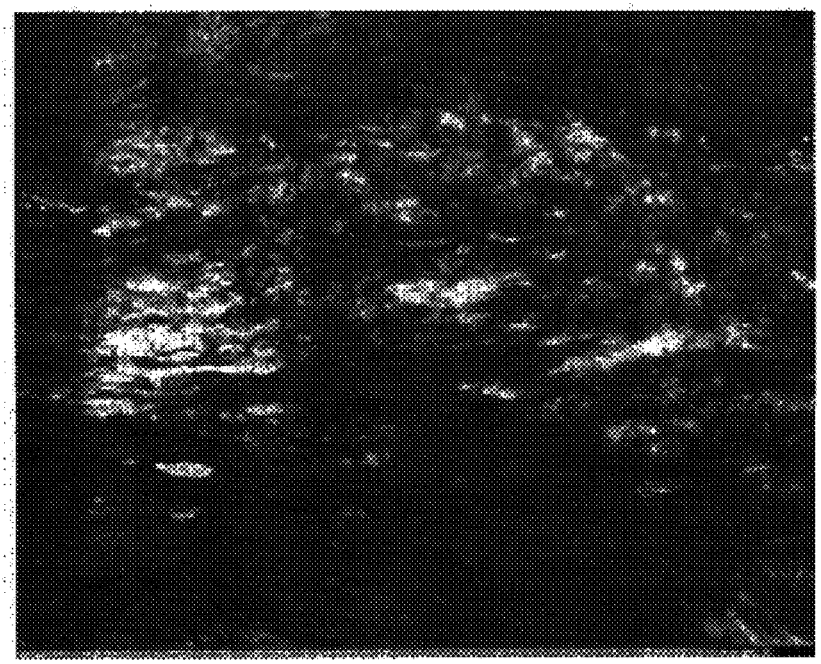

Results:

As shown in FIG. 9, red stain indicated nerve fiber regeneration, which was mostly seen in the nerve tissue of the GASP treatment group (FIG. 9(B)) and markedly less in that of the control group (FIG. 9(A)). This indicates that the GASP was effective in promoting nerve fiber regeneration in rats after the sciatic nerve was cut-off, followed by re-stitching of the outer layers of the sciatic nerve.

Conclusion

It had been demonstrated that GASP was effective in promoting nerve fiber regeneration after a crush nerve injury.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A method for treating a mammal with spinal cord injury comprising:

administering an effective amount of sporoderm-broken germination activated *Ganoderma* spores (GASP) to a mammal having spinal cord injury, wherein said GASP are prepared by:

soaking *Ganoderma* spores in a solution to cause said *Ganoderma* spores to germinate, placing said germinated *Ganoderma* spores in a culture box at a relative humidity of 65–98% and a temperature of 18–48° C. to cause said germinated *Ganoderma* spores to activate; and breaking said germination activated *Ganoderma* spores with an enzyme with cell wall dissolving property or with a mechanical force to produce said GASP.

2. The method according to claim 1, wherein said GASP are orally administered to said mammal.

3. The method according to claim 1, wherein said GASP are administered to said mammal within about 1 day of said spinal cord injury.

4. The method according to claim 1, wherein said mammal is human.

5. The method according to claim 1, wherein said spinal cord injury is caused by compression or severance of the spinal cord.

6. The method according to claim 1, wherein said spinal cord injury is caused by a trauma.

7. The method according to claim 5, wherein the spinal cord injury is caused by severance of a ventral root of the spinal cord.

8. The method according to claim 5, wherein the spinal cord injury is caused by severance or crush of the sciatic nerve.

9. The method according to claim 1, wherein said spinal cord injury is caused by a disease.

10. The method according to claim 9, wherein said disease is polio, spina bifida, or Friedreich's Ataxia.

11. The method according to claim 1, wherein said spinal cord injury is caused by damage or death of neurons within said injured spinal cord.

12. The method according to claim 11, wherein said neurons are motor neurons.

13. The method according to claim 1, wherein said spinal cord injury is caused by crush of axons with said injured spinal cord.

14. The method according to claim 1, wherein said effective amount of said GASP is about 0.5–15 g per kg of body weight per day.

15. A method for improving survival of neurons after a spinal cord injury comprising:

administering an effective amount of GASP to a mammal having said spinal cord injury, wherein said GASP are prepared by:

soaking *Ganoderma* spores in a solution to cause said *Ganoderma* spores to germinate, placing said germinated *Ganoderma* spores in a culture box at a relative humidity of 65–98% and a temperature of 18–40° C. to cause said germinated *Ganoderma* spores to activate; and breaking said germination activated *Ganoderma* spores with an enzyme with cell wall dissolving property or with a mechanical force to produce said GASP.

16. The method according to claim 15, wherein said mammal is human.

17. The method according to claim 15, wherein said GASP are administered to said mammal within 1 day of said spinal cord injury.

18. The method according to claim 15, wherein said neuron is a motor neuron in said injured spinal cord.

19. The method according to claim 15, wherein said effective amount of said GASP is about 0.5–15 g per kg of body weight per day.

20. A method for promoting axon regeneration in a spinal cord injury comprising:

administering an effective amount of GASP to a mammal having said spinal cord injury, wherein said GASP are prepared by:

soaking *Ganoderma* spores in a solution to cause said *Ganoderma* spores to germinate, placing said germinated *Ganoderma* spores in a culture box at a relative humidity of 65–98% and a temperature of 18–40° C. to cause said germinated *Ganoderma* spores to activate; and breaking said germination activated *Ganoderma* spores with an enzyme with cell wall dissolving property or with a mechanical force to produce said GASP.

21. The method according to claim 20, wherein said GASP are administered to said mammal within 1 day of said spinal cord injury.

22. The method according to claim 20, wherein said effective amount of said GASP is about 0.5–15 g per kg of body weight per day.

* * * * *